(12) United States Patent
Hwang et al.

(10) Patent No.: US 7,723,106 B2
(45) Date of Patent: May 25, 2010

(54) STROMA-FREE, SERUM-FREE, AND CHEMICALLY DEFINED MEDIUM AND METHOD FOR EX VIVO MONONUCLEAR CELL EXPANSION USING THE SAME

(75) Inventors: Shiaw-Min Hwang, Hsinchu (TW); Chao-Ling Yao, Tainan (TW); Tzu-Bou Hsieh, Hsinchu (TW); I-Ming Chu, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 548 days.

(21) Appl. No.: 11/192,960

(22) Filed: Jul. 29, 2005

(65) Prior Publication Data

US 2006/0024827 A1 Feb. 2, 2006

(51) Int. Cl.
*C12N 5/00* (2006.01)
*C12N 5/02* (2006.01)
(52) U.S. Cl. .................. 435/325; 435/404; 435/405; 435/406; 435/407; 435/408
(58) Field of Classification Search ............. 435/325, 435/404, 405, 406, 407, 408
See application file for complete search history.

(56) References Cited

U.S. PATENT DOCUMENTS

| | | | | |
|---|---|---|---|---|
| 5,610,056 | A | * | 3/1997 | Nakahata ............... 435/378 |
| 5,744,347 | A | * | 4/1998 | Wagner et al. .......... 435/354 |
| 6,225,119 | B1 | * | 5/2001 | Qasba et al. ............ 435/373 |
| 2002/0006663 | A1 | * | 1/2002 | Scadden et al. ......... 435/455 |
| 2005/0272152 | A1 | * | 12/2005 | Xu et al. ................. 435/372 |

FOREIGN PATENT DOCUMENTS

EP 1424388 A1 6/2004

OTHER PUBLICATIONS

Claassen et al., "A cell culture system that enhances mononuclear cell IgE synthesis indunced by recombinant human interleukin 4", J Immuno Meth, Feb. 9, 1990; 126 (2):213-22, abstract.*
U.S. Appl. No. 10/909,370.*
"Factorial Designs Combined with the Steepest Ascent Method to Optimize Serum-Free Media for Ex Vivo Expansion of Human Hematopoietic Progenitor Cells" Yao et al., 02/2203.

* cited by examiner

*Primary Examiner*—Ruth A Davis
(74) *Attorney, Agent, or Firm*—Thomas, Kayden, Horstemeyer & Risley (57) ABSTRACT

A stroma-free, serum-free, and chemically defined medium and a method for mononuclear cell expansion ex vivo using the same. An exemplary medium includes a basal medium, a serum substitute, and a cytokine formula.

11 Claims, 6 Drawing Sheets

STROMA-FREE, SERUM-FREE, AND CHEMICALLY DEFINED MEDIUM AND METHOD FOR EX VIVO MONONUCLEAR CELL EXPANSION USING THE SAME

BACKGROUND

The invention relates to mononuclear cell expansion, and more particularly, to ex vivo expansion of hematopoietic stem cells (HSCs) derived from umbilical mononuclear cells.

All mature blood cells originate from a small population of hematopoietic stem cells (HSCs), which are characterized by their capacities to self-renew and the ability to differentiate into different hematopoietic cell lineages [Moore K A, et al. Blood. 1997; 89:4337-4347; McAdams T A, et al. Trends Biotechnol. 1996; 14:341-349]. The CD34 antigen, an integral membrane glycoprotein that functions as a regulator of hematopoietic cell adhesion to stromal cells within the marrow microenvironment, is expressed on human HSCs [Baum C M, et al. Proc Natl Acad Sci USA. 1992; 89:2804-2808; Guzman P F, et al. Arch Med Res. 2002; 33:107-114]. Cells that express high amount of CD34 antigen are described as early multipotential colony-forming unit (CFU)-Mix, CFU-blast and long-term culture-initiating cells (LTC-ICs), and their morphology appears as lymphocyte-like cells [Prosper F, et al. Blood. 1997; 89:3991-3997; Shih C C, et al. Blood. 1999; 94:1623-1636]. In clinical application, the number of $CD34^+$ cells infused proved to be the major prognostic factor for engraftment and survival [Moore K A, et al. Blood. 1997; 89:4337-4347; McAdams T A, et al. Trends Biotechnol. 1996; 14:341-349; Shih C C, et al. Blood. 1999; 94:1623-1636]. Additionally, more and more studies have demonstrated that the $CD34^+CD38^-$ fraction contains most clonogenic cells that can repopulate nonobese diabetic/severe combined immunodeficient (NOD/SCID) mice [Danet G H, et al. Exp Hematol. 2001; 29:1465-1473; Zandstra P W, et al. Proc Natl Acad Sci USA. 1997; 94:4698-4703; Bhatia M, et al. Proc Natl Acad Sci USA. 1997; 94:5320-5325].

Umbilical cord blood (UCB), collected from the postpartum placenta and cord, has been identified as a rich source of HSCs, and provided as alternative to bone marrow transplantation [Gluckman E, et al. Bone Marrow Transplant. 1998; 22:68-74]. UCB transplantation has been used for treating hematopoietic disorders (leukemia, anemia, etc.), congenital immunodeficiencies, metabolic disorders, and autoimmune diseases [Rubinstein P, et al. N Engl J Med. 1998; 339:1565-1577; Kurtzberg J, et al. N Engl J Med. 1996; 335:157-166]. UCB transplantation in adults, however, has been limited by the concern that a single UCB unit does not contain sufficient number of $CD34^+$ cells (the optimal dose for an adult is $\geq 2.5 \times 10^6$ $CD34^+$ cells/kg) to rapidly reconstitute adult bone marrow function [Gilmore G L, et al. Exp Hematol. 2000; 28:1297-1305; McNiece I, et al. Exp Hematol. 2001; 29:3-11; McAdams T A, et al. Trends Biotechnol. 1996; 14:388-396]. Consequently, it is desirable if HSCs expansion ex vivo can be developed empirically without loss of their engraftment ability.

The dynamics of hematopoiesis are regulated by a delicate interplay of molecular signal and cellular microenvironment. Molecular signaling among cells is mainly achieved by means of secreted glycoproteins, also known as cytokines. One cytokine might have different effects on different types of cells, depending on the target cells, its concentration, and the presence of other cytokines [Guzman P F, et al. Arch Med Res. 2002; 33:107-114; Zandstra P W, et al. Proc Natl Acad Sci USA. 1997; 94:4698-4703; Gilmore G L, et al. Exp Hematol. 2000; 28:1297-1305; Yonemura Y, et al. Blood. 1997; 89:1915-1921; Lebkowski J S, et al. Stem Cells. 1995; 13:607-612; Audet J, et al. Biotechnol Bioeng. 2002; 80:393-404; Yao C L, et al. Enzyme Micro Technol. 2003; 33:343-352]. The cellular microenvironment, which is composed of stromal cells within bone marrow, is responsible for the fixation of HSCs by adhesion molecules, and also for the stromal cells secreted cytokines that promote HSC proliferation and differentiation [Baum C M, et al. Proc Natl Acad Sci USA. 1992; 89:2804-2808; Guzman P F, et al. Arch Med Res. 2002; 33:107-114; Prosper F, et al. Blood. 1997; 89:3991-3997; Shih C C, et al. Blood. 1999; 94:1623-1636; Yoo E S, et al. Stem Cells. 2003; 21:228-235; Rosler E, et al. Exp Hematol. 2000; 28:841-852]. However, the allogeneic or xenogeneic stromal cells in the co-culture system may induce immunoresponses when the ex vivo expanded HSCs are infused into patients. Serum, commonly used to support the culture of HSCs in many studies [Guzman P F, et al. Arch Med Res. 2002; 33:107-114; Prosper F, et al. Blood. 1997; 89:3991-3997; Shih C C, et al. Blood. 1999; 94:1623-1636; Gilmore G L, et al. Exp Hematol. 2000; 28:1297-1305; Yonemura Y, et al. Blood. 1997; 89:1915-1921], contains growth-required compounds including hormones, growth factors and binding proteins. However, serum is a potential source of bacterial, mycoplasmal and viral contaminations. Many reports have tried to develop serum-free media for ex vivo expansion of hematopoietic cells [Koller M R, et al. J Hematother. 1998; 7:413-423; Sandstrom C E, et al. Biotechnol Bioeng. 1994; 43:706-733; Mobest D, et al. Biotechnol Bioeng. 1998; 60:341-347; Bruyn C D, et al. Cytotherapy. 2003; 5:153-160]. To better conform to the clinical regulations, a stroma-free, serum-free, and chemically defined medium must be developed for HSCs expansion ex vivo.

SUMMARY

A two-level factorial design has been proven effectively for developing microbial and animal cell media [Liu C H, et al. Biotechnol Lett. 1994; 16:801-806; Liu C H, et al. Enzyme Microb Technol. 2001; 28:314-321; Chen K C, et al. Enzyme Microb Technol. 1992; 14:659-664; and Chang Y N, et al. Enzyme Microb Technol. 2002; 30:889-894]. This system is a powerful technique for testing multiple component variables because its implementation requires fewer experimental trials than other techniques. The inventors have previously developed a serum-free medium for HSC expansion based on isolated $CD34^+$ cells from UCB [Yao C L, et al. Enzyme Micro Technol. 2003; 33:343-352], however, the operating procedure of $CD34^+$ cell isolation is costly and time-consuming. Based on the previously developed serum-free medium, the inventors developed an improved ex vivo expansion medium which specifically stimulate $CD34^+$ cells proliferation in mononuclear cell (MNC) culture system, and the invention is, thus, achieved.

It is, therefore, provided, a stroma-free, serum-free, and chemically defined medium for ex vivo mononuclear cell expansion. The medium comprises a basal medium, a serum substitute, and a cytokine formula.

In one embodiment of the stroma-free, serum-free, and chemically defined medium for ex vivo mononuclear cell expansion, the basal medium can be, but is not limited to, Iscove's modified Dulbecco's medium (IMDM), McCoy's 5A medium, minimum essential medium alpha medium (α-MEM), or F-12K nutrient mixture medium (Kaighn's modification, F-12K), preferably IMDM.

In another embodiment of the stroma-free, serum-free, and chemically defined medium for ex vivo mononuclear cell expansion, the serum substitute includes bovine serum albumin (BSA), insulin, and transferrin (TF).

In the other embodiment of the stroma-free, serum-free, and chemically defined medium for ex vivo mononuclear cell expansion, the cytokine formula includes thrombopoietin (TPO), stem cell factor (SCF), stem cell growth factor-α (SCGF), Flt-3 ligand (FL), interleukin (IL)-3, IL-6, IL-11, granulocyte colony-stimulating factor (G-CSF), and granulocyte-macrophage colony-stimulating factor (GM-CSF).

A method for mononuclear cell expansion ex vivo is also provided. The method includes the steps of: providing an initiating mononuclear cell; culturing the mononuclear cell in the stroma-free, serum-free, and chemically defined medium as above described; and collecting the expanded mononuclear cell.

In one embodiment of the method for mononuclear cell expansion ex vivo, the initiating mononuclear cell is a hematopoietic stem cell derived from umbilical cord blood (UCB). The expanded mononuclear cell is a hematopoietic stem cell, and the hematopoietic stem cell is $CD34^+$ cell.

BRIEF DESCRIPTION OF THE DRAWINGS

A stroma-free, serum-free, and chemically defined medium and a method for ex vivo mononuclear cell expansion using the same can be more fully understood and further advantages become apparent when reference is made to the following description and the accompanying drawings in which:

FIGS. 3A~3D illustrates flow cytometry analysis of surface antigen expression (CD34 and CD38) before and after expansion of cells.

DETAILED DESCRIPTION

A stroma-free, serum-free, and chemically defined medium and a method for ex vivo mononuclear cell expansion using the same are provided.

The inventors have previously reported a serum-free medium for $CD34^+$ cell expansion by using purified $CD34^+$ cells from UCB [Yao C L, et al. Enzyme Micro Technol. 2003; 33:343-352]. There are many commercially available kits that can isolate $CD34^+$ cells from MNC, however, skipping the CD34 isolation will simplify the processing and reduce the cost for clinical applications. Consequently, the inventors tried to develop a serum-free and cytokine-containing medium for expanding human $CD34^+$ cell population directly in the MNC culture system. A two-level factorial design combined with steepest ascent method, a powerful technique in medium development for screening ingredient variables and optimizing their concentrations, was applied. A serum-free medium, denominated as SF-MNC, for $CD34^+$ cells ex vivo expansion in the MNC culture system was developed by the statistic methodology. SF-MNC medium includes Iscove's modified Dulbecco's medium (IMDM) with BIT (BSA, insulin, and transferrin) and CC-9 (TPO, IL-3, SCF, FL, IL-6, G-CSF, GM-CSF, SCGF, and IL-11). The most important serum substitute and cytokine are BSA and SCF, respectively. The expansion results in SF-MNC medium shows that most increasing cells were $CD34^+CD38^-$ cells, not mature WBCs. It means that HSCs could be maintained, expanded and less differentiated in SF-MNC culture system. Comparing with previous literatures or commercial media, SF-MNC had lower cytokine concentrations, but superior or comparable expansion ability on $CD34^+$ cell and CFC growth.

Ex vivo expansion of HSCs is important in clinical applications, including stem cell transplantation, gene therapy, and tumor cell purging. Although the reagents and cytokines must be approved in clinical or cGMP grade for clinical usage, the experimental results demonstrated that the statistic methodology to this approach was valid. The goal of developing a clinically suitable medium for expanding cord blood HSCs ex vivo appears feasible, and should be beneficial to patients requiring an autologous or allogeneic transplant.

It is, therefore, provided a stroma-free, serum-free, and chemically defined medium for ex vivo mononuclear cell expansion. The medium includes a basal medium, a serum substitute, and a cytokine formula.

In one embodiment of the stroma-free, serum-free, and chemically defined medium, the basal medium can be, but is not limited to, Iscove's modified Dulbecco's medium (IMDM), McCoy's 5A medium, minimum essential medium alpha medium (α-MEM), or F-12K nutrient mixture medium (Kaighn's modification, F-12K); preferably IMDM.

In the other embodiment of the stroma-free, serum-free, and chemically defined medium, the serum substitute includes bovine serum albumin (BSA), insulin, and transferrin (TF). Specifically, the serum substitute includes 0.1~50 g/l BSA, 0.01~1000 µg/ml insulin, and 0.1~1000 µg/ml transferrin; preferably, 0.1~10 g/l BSA, 0.01~10 µg/ml insulin, and 0.1~400 µg/ml transferrin; more preferably, the serum substitute includes 4 g/l BSA, 0.71 µg/ml insulin, 27.81 µg/ml transferrin.

In another embodiment of the stroma-free, serum-free, and chemically defined medium, the cytokine formula includes thrombopoietin (TPO), stem cell factor (SCF), stem cell growth factor-α (SCGF), Flt-3 ligand (FL), interleukin (IL)-3, IL-6, IL-11, granulocyte colony-stimulating factor (G-CSF), and granulocyte-macrophage colony-stimulating factor (GM-CSF). Specifically, the cytokine formula includes 0.1~500 ng/ml TPO, 0.1~500 ng/ml SCF, 0.1~500 ng/ml SCGF, 0.1~500 ng/ml FL, 0.1~500 ng/ml IL-3, 0.1~500 ng/ml IL-6, 0.1~500 ng/ml IL-11, 0.1~500 ng/ml G-CSF, and 0.1~500 ng/ml GM-CSF; preferably, the cytokine formula includes 0.1~100 ng/ml TPO, 0.1~100 ng/ml SCF, 0.1~100 ng/ml SCGF, 0.1~100 ng/ml FL, 0.1~100 ng/ml IL-3, 0.1~100 ng/ml IL-6, 0.1~100 ng/ml IL-11, 0.1~100 ng/ml G-CSF, and 0.1~100 ng/ml GM-CSF; more preferably, the cytokine formula includes 5.53 ng/ml TPO, 16 ng/ml SCF, 2.64 ng/ml SCGF, 4.43 ng/ml FL, 2.03 ng/ml IL-3, 2.36 ng/ml IL-6, 0.69 ng/ml IL-11, 1.91 ng/ml G-CSF, and 1.56 ng/ml GM-CSF.

In a preferred embodiment of the stroma-free, serum-free, and chemically defined medium, the medium includes a basal medium of IMDM, a serum substitute composed of bovine serum albumin (BSA), insulin, and transferring (TF), and a cytokine formula including TPO, IL-3, SCF, FL, IL-6, G-CSF, GM-CSF, SCGF, and IL-11.

A method for mononuclear cell expansion ex vivo is also provided. The method includes the steps of providing an initiating mononuclear cell, culturing the mononuclear cell in a stroma-free, serum-free, and chemically defined medium as above described; and collecting the expanded mononuclear cell.

In one embodiment of the method for mononuclear cell expansion ex vivo, the initiating mononuclear cell is a hematopoietic stem cell. In addition, the expanded mononuclear cell is a hematopoietic stem cell, and the hematopoietic stem cell is $CD34^+$ cell.

In the examples, mononuclear cells (MNCs) as starting culture cells were isolated from umbilical cord blood (UCB). HSCs were stimulated to proliferate ex vivo in the MNC culture system with variable serum substitutes, cytokines, and basal media according to experimental design. The expanded cells were assessed for cellular characteristics by surface antigen analysis, colony-forming cell assay (CFC assay), and long-term culture-initiating cell assay (LTC-IC assay). The results show that the optimal compositions of serum substitutes and the cytokine cocktail for HSC expansion in the MNC culture system were BIT (4 g/l BSA, 0.71 μg/ml insulin, and 27.81 μg/ml transferrin), and CC-9 (5.53 ng/ml TPO, 2.03 ng/ml IL-3, 16 ng/ml SCF, 4.43 ng/ml FL, 2.36 ng/ml IL-6, 1.91 ng/ml G-CSF, 1.56 ng/ml GM-CSF, 2.64 ng/ml SCGF, and 0.69 ng/ml IL-11) in the Iscove's modified Dulbecco's medium. After 6-day culture, the absolute fold expansions for white blood cells, $CD34^+$ cells, $CD34^+CD38^-$ cells, CFC, and LTC-IC were 1.4-, 30.4-, 63.9-, 10.7-, 2.8-fold, respectively.

Using the statistic methodology to develop HSC expansion medium, the formula had lower cytokine concentrations comparing to other literatures and commercial media, but had superior or comparable expansion ability on HSC growth.

Practical examples are described herein.

EXAMPLES

Material and Methods

UCB Samples Collection and MNC Processing

The term UCB was harvested with a standard 250-ml blood bag (Terumo, Shibuya-ku, Tokyo, Japan) with the informed consent and processed within 24 hrs. Buffy coat cells were obtained from UCB by centrifugation (700×g, 20 mins), and were diluted with an equal volume of wash buffer (Dulbecco's phosphate buffered saline, D-PBS, containing 2 mM EDTA, Sigma, St. Louis, Mo.). Then the cells were layered onto Ficoll-Paque solution ($\rho$=1.077 g/ml, Amersham Biosciences, Uppsala, Sweden) and centrifuged to deplete red blood cells, platelets and plasma (700×g, 40 mins). MNCs were collected, and washed with D-PBS twice. Recovery rate, viability, percentage of $CD34^+$ fraction, colony-forming cells (CFCs), and long-term culture-initiating cells (LTC-ICs) were determined as day 0 for control. For expansion, MNC were seeded at a concentration of $5\times10^5$ cells/ml in 24-well plates with variable serum substitutes and cytokines according to experiment design (all experiments were repeated at least six times).

Cytokines

The following recombinant human cytokines were used: thrombopoietin (TPO), stem cell factor (SCF), stem cell growth factor-α (SCGF), Flt-3 ligand (FL), interleukin (IL)-3, IL-6, IL-11, granulocyte-macrophage colony-stimulating factor (GM-CSF), granulocyte colony-stimulating factor (G-CSF), and hepatocyte growth factor (HGF) were all purchased from PeproTech EC Ltd. (London, UK).

Chemicals and Media

The following chemicals were used: bovine serum albumin (BSA), and insulin were purchased from Sigma. Transferrin and 2-mercaptoethanol (2-ME) were purchased from GIBCO (Carlsbad, Calif.). The following basal media were used: Iscove's modified Dulbecco's medium (IMDM), RPMI 1640 medium, McCoy's 5A medium, minimum essential medium alpha medium (α-MEM), basal medium Eagle (BME), Dulbecco's modified Eagle medium (DMEM), Fischer's medium, Medium 199 and F-12K nutrient mixture medium (Kaighn's modification, F-12K) were purchased from GIBCO. X-vivo 20™ medium was purchased from BioWhittaker (Walkersville, Mass.). Stemline™ Hematopoietic stem cell expansion medium (Stemline) was purchased from Sigma. Stemspan™ H2000 contained Stemspan™ CC100 medium (cytokine cocktail of 100 ng/ml FL, 100 ng/ml SCF, 20 ng/ml IL-3 and 20 ng/ml IL-6) (H2000+CC100) was purchased from StemCell Technologies. (Vancouver, Canada).

Colony-Forming Cell Assay (CFC Assay)

Before and after expanding culture, cells were plated in semisolid culture (MethoCult™ GF H4434, StemCell Technologies.) following the manufacturer's instruction for colony-forming unit assay. The cells were seeded at suitable concentration (to give <100 colonies per 1 ml culture). Methylcellulose based media were aliquotted in 35 mm petri dishes and incubated at 37° C. in an atmosphere of 5% $CO_2$ and humidified incubator. After 14 days of culture, burst-forming unit-erythroid (BFU-E), colony-forming unit-granulocyte/macrophage (CFU-GM), and colony-forming unit-granulocyte/erythroid/macrophage/megakaryocyte (CFU-GEMM) were scored under inverted microscope.

Long-Term Culture-Initiating Cell Assay (LTC-IC Assay)

The murine fibroblast cell line M2-10B4 (BCRC 60228, Bioresource Collection and Research Center, Taiwan) was used as feeder layer. One day before initiation of co-culture with human cells, M2-10B4 cells were incubated with 20 μg/ml mitomycin C (Sigma) for 3 hrs [Ponchio L, et al. Cytotherapy. 2000; 2:281-286], trypsinized, and seeded into gelatin-coated 24-well plates ($7.5\times10^4$/well). Cells before or after expanding culture ($5\times10^5$ cells) were plated in 8 replicate wells with M2-10B4 cell as feeder layer in 1 ml of Myelocult™ H5100 (StemCell Technologies) supplemented with 10-6 M hydrocortisone (Sigma). The plates were incubated at 37° C., 5% $CO_2$ for 5 weeks. At weekly intervals, half the culture medium was removed and replaced with fresh culture medium. At the end of the culture period, nonadherent cells were combined with the corresponding trypsinized adherent cells, washed, and assayed for CFC as described above.

Flow Cytometry Analysis of Surface Antigen Expression

Before and after expanding culture, cells were analyzed by two-color flow cytometry on a FACSCaliber analyzer (Becton-Dickinson, San Jose, Calif.). About $1\times10^6$ cells were stained with FITC-conjugated anti-human CD45 or CD38, and PE-conjugated anti-human CD34, and gated for $CD45^+$ $CD34^+$ or $CD34^+CD38^-$ cells with low side scatter, according to the CD34 enumeration protocols developed by the International Society of Hematotherapy and Graft Engineering (ISHAGE) [Sutherland D R, et al. J Hematother. 1996; 5:231-8]. A replicate sample was stained with FITC-mouse IgG1 and PE-mouse IgG1 as an isotype control to ensure specificity.

Experimental Aesign and Statistical Analysis

Two-level factorial design followed the method of steepest ascent was carried out to find the optimal concentrations of serum substitutes and cytokines for $CD34^+$ cells expansion. Fractional and full factorial design data were regressed by SPSS software to obtain the first order polynomial. Its statistic significance was determined by an F-test and the significance of the regression coefficients was analyzed by a t-test. The polynomial takes the form of White blood cells (WBCs)/ml or CD34$^+$ cells /ml=$\alpha_0+\alpha_i x_i$     (1)

where $\alpha$'s are the fitted constants and x's are coded variables for the tested additives.

The regression model can identify the most effective ingredients and can give the information to construct the steepest ascent path to obtain the optimal medium composition for CD34$^+$ cells expansion in the MNC culture system. In the screening tests, the magnitude and sign of the regression constants can be used to identify the significance of the variables on responses such as CD34$^+$ cell density. If the coefficient is relatively large, it has more significant effect on the response as compared to the small one does. Furthermore, the variable with positive fitted constant is helpful to the response and that one with negative coefficient has inhibitory effects on the response. Besides, the coefficients of model can be used to construct the steepest ascent path. The direction of the maximal increase in cell density is yielded by the gradient of the regressed polynomial. Experiments were conducted along the steepest ascent path to obtain the optimal medium composition for CD34$^+$ cell growth.

The strategy of developing serum-free and cytokine-containing media was as follows: (1) to determine the optimal concentration of serum substitutes in the IMDM; (2) to determine the optimal concentration of cytokine combinations in the IMDM containing serum substitutes; (3) compare the formulation with those using other basal media (i.e. not IMDM) and those commercially available media.

Example 1

Characteristics of the MNC Isolation From UCB

Over 100 units of UCB were isolated. The average sample volume was 144 ml (112-176 ml, including 35 ml anticoagulant), containing an average of $1.71\times10^9$ WBCs ($0.97$-$2.37\times 10^9$ WBCs). After Ficoll-Paque density gradient centrifugation, the average recovery rate of MNCs was 32.42% (23.13-45.89%), and the fraction of CD34$^+$ cells, CFC, LTC-IC, and CD34$^+$CD38$^-$ cells in MNCs was 0.81% (0.39-1.74%), 0.71% (0.14-2.54%), 0.05% (0.02-0.11%), and 0.29% (0.18-0.64%), respectively.

Example 2

Serum Substitutes Screening

As has been extensively reviewed [Sandstrom C E, et al. Biotechnol Bioeng. 1994; 43:706-733; Mobest D, et al. Biotechnol Bioeng. 1998; 60:341-347; Bruyn C D, et al. Cytotherapy. 2003; 5:153-160] and based on the inventors' previous experience [Lebkowski J S, et al. Stem Cells. 1995; 13:607-612; Audet J, et al. Biotechnol Bioeng. 2002; 80:393-404; Yao C L, et al. Enzyme Micro Technol. 2003; 33:343-352], four kinds of compounds that are frequently used as serum substitutes were selected—bovine serum albumin (BSA), insulin, transferring (TF), and 2-mercaptoethanol (2-ME). The $2^4$ full factorial design was adopted to determine which serum substitutes were required for CD34$^+$ cell expansion in the MNC culture system. The $2^4$ full factorial design could efficiently test four compounds with 16 trials and provide completely degrees of freedom to obtain the coefficients. The basal medium was IMDM (Iscove's modified Dulbecco's medium) containing a cocktail of seven cytokines (8.46 ng/ml TPO, 4.09 ng/ml IL-3, 15 ng/ml SCF, 6.73 ng/ml FL, 0.78 ng/ml IL-6, 3.17 ng/ml G-CSF, and 1.30 ng/ml GM-CSF), which had been demonstrated for an optimal formula of pure CD34$^+$ cell expansion [Yao C L, et al. Enzyme Micro Technol. 2003; 33:343-352]; the initial cell density was $5\times10^5$ MNCs/ml and the cells were analyzed after 7-day culture.

Table 1 lists the coded level of each serum substitute, WBC growth and CD34$^+$ cell growth.

TABLE 1

Matrix of the $2^4$ full factorial design and experiment results*

| Trial | BSA (10 g/l) | Insulin (10 μg/ml) | TF (0.4 g/l) | 2-ME (55 μM) | WBC† ($10^5$/ml) | CD34$^+$ cell† ($10^4$/ml) |
|---|---|---|---|---|---|---|
| 1 | −1 | −1 | −1 | −1 | 1.5 | 0.77 |
| 2 | +1 | −1 | −1 | −1 | 4.8 | 10.00 |
| 3 | −1 | +1 | −1 | −1 | 1.5 | 0.56 |
| 4 | +1 | +1 | −1 | −1 | 8.5 | 13.37 |
| 5 | −1 | −1 | +1 | −1 | 2.0 | 1.72 |
| 6 | +1 | −1 | +1 | −1 | 5.0 | 10.26 |
| 7 | −1 | +1 | +1 | −1 | 3.3 | 2.17 |
| 8 | +1 | +1 | +1 | −1 | 7.8 | 13.23 |
| 9 | −1 | −1 | −1 | +1 | 1.0 | 0.64 |
| 10 | +1 | −1 | −1 | +1 | 4.5 | 8.29 |
| 11 | −1 | +1 | −1 | +1 | 1.5 | 0.57 |
| 12 | +1 | +1 | −1 | +1 | 7.5 | 10.85 |
| 13 | −1 | −1 | +1 | +1 | 2.3 | 1.75 |
| 14 | +1 | −1 | +1 | +1 | 5.0 | 10.70 |
| 15 | −1 | +1 | +1 | +1 | 3.5 | 1.86 |
| 16 | +1 | +1 | +1 | +1 | 7.3 | 13.70 |

*−1: no addition; +1: adding the indicated amount of additives; the initial seed density was $5\times10^5$ cells/ml.
†Cell density at day 7.

The results of the linear first-order models were regressed according to the data listed in Table 1.

WBCs/mL($\times10^5$)=4.17+2.11$x_1$+0.92$x_2$+0.33$x_3$−0.11$x_4$     (2)

CD34$^+$ cells/mL ($\times10^4$)=6.28+5.02$x_1$+0.76$x_2$+0.65$x_3$−0.23$x_4$     (3)

Where $x_1$, $x_2$, $x_3$, and $x_4$ are coded variables of BSA, insulin, TF, and 2-ME, respectively. Both Eq. (2) and Eq. (3) indicated that BSA, insulin, and TF could enhance the growth of WBCs and CD34$^+$ cells, since these serum substitutes had positive coefficients in the first order polynomials. However, 2-ME would inhibit WBC and CD34$^+$ cell growth owing to its negative coefficient. The main factor for WBC and CD34$^+$ cells growth was BSA, which had the largest positive coefficient.

A steepest ascent path for CD34$^+$ cell growth was designed to obtain the optimal concentrations of BSA, insulin, and TF for the serum-free medium, as shown in Table 2.

TABLE 2

The concentrations of serum substitutes along the steepest ascent path for WBC and CD34$^+$ cell growth in the serum-free medium*

| Step | BSA (g/L) | Insulin (μg/ml) | TF (μg/ml) | WBC† ($10^5$/ml) | CD34$^+$ cell† ($10^4$/ml) |
|---|---|---|---|---|---|
| 1 | 0 | 0 | 0 | 1.52 (0.14) | 0.77 (0.09) |
| 2 | 0.2 | 0.04 | 1.39 | 5.72 (0.23) | 5.90 (0.22) |
| 3 | 0.4 | 0.07 | 2.78 | 5.58 (0.24) | 6.72 (0.28) |
| 4 | 0.6 | 0.11 | 4.17 | 6.21 (0.28) | 7.39 (0.30) |
| 5 | 0.8 | 0.14 | 5.56 | 5.95 (0.25) | 7.63 (0.29) |
| 6 | 1.0 | 0.18 | 6.95 | 6.41 (0.35) | 8.26 (0.35) |
| 7 | 2.0 | 0.36 | 13.91 | 6.90 (0.22) | 8.98 (0.38) |
| 8 | 3.0 | 0.53 | 20.86 | 6.90 (0.17) | 9.53 (0.41) |
| 9 | 4.0 | 0.71 | 27.81 | 7.32 (0.24) | 13.03 (0.51) |

TABLE 2-continued

The concentrations of serum substitutes along the steepest ascent path for WBC and CD34+ cell growth in the serum-free medium*

| Step | BSA (g/L) | Insulin (μg/ml) | TF (μg/ml) | WBC† (10⁵/ml) | CD34+ cell† (10⁴/ml) |
|---|---|---|---|---|---|
| 10 | 5.0 | 0.89 | 34.76 | 6.94 (0.31) | 12.11 (0.43) |
| 11 | 6.0 | 1.07 | 41.72 | 6.99 (0.28) | 10.54 (0.38) |
| 12 | 7.0 | 1.25 | 48.67 | 6.72 (0.31) | 9.04 (0.33) |
| 13 | 8.0 | 1.42 | 55.62 | 6.11 (0.34) | 8.42 (0.28) |
| 14 | 9.0 | 1.60 | 62.58 | 6.92 (0.29) | 10.36 (0.45) |
| 15 | 10.0 | 1.78 | 69.53 | 6.72 (0.28) | 10.37 (0.44) |

*Value in the parenthesis was the standard deviation; the initial seed density was $5 \times 10^5$ cells/ml.
†Cell density at day 7.

According to their coefficients of Eq. (3), WBC and CD34+ cell densities increased with the experiment step, and then plateaued in step 9 (Table 2). After that, WBC and CD34+ cell densities declined step by step. Consequently, the concentration of the serum substitute formula was optimized and named BIT (serum substitutes cocktail: 4 g/l BSA, 0.71 μg/ml insulin, and 27.81 μg/ml TF) for CD34+ cell expansion in MNC culture system.

Example 3

Cytokines Screening

Hematopoietic cytokines belong to a large and growing family of glycoproteins that are necessary for ex vivo expansion of hematopoietic cells [Yonemura Y, et al. Blood. 1997; 89:1915-1921; Lebkowski J S, et al. Stem Cells. 1995; 13:607-612]. Cytokine effect is complex, but crucial for the success of the culture owing to the dosage effect, and the synergistic and inhibitive interactions among the cytokines. Ten kinds of cytokines generally used for expanding HSCs were chosen. SCF and FL are essential for survival and proliferation, and can prevent apoptosis of early progenitor cells [Moore K A, et al. Blood. 1997; 89:4337-4347; McAdams T A, et al. Trends Biotechnol. 1996; 14:341-349; Danet G H, et al. Exp Hematol. 2001; 29:1465-1473]. SCGF functions like SCF and FL [McAdams T A, et al. Trends Biotechnol. 1996; 14:341-349]. IL-3 is an important growth factor to hematopoiesis [Prosper F, et al. Blood. 1997; 89:3991-3997; Shih C C, et al. Blood. 1999; 94:1623-1636; McNiece I, et al. Exp Hematol. 2001; 29:3-11]. IL-6 is a nonspecific, early-acting hematopoietic growth factor that can induce the cycling of HSCs [Moore K A, et al. Blood. 1997; 89:4337-4347; Guzman P F, et al. Arch Med Res. 2002; 33:107-114; Shih C C, et al. Blood. 1999; 94:1623-1636; Yonemura Y, et al. Blood. 1997; 89:1915-1921]. IL-11 can regulate the differentiation and proliferation of megakaryocyte progenitors as well as primitive HSC [Yonemura Y, et al. Blood. 1997; 89:1915-1921]. G-CSF can promote the development of neutrophilic granulocytes [Guzman P F, et al. Arch Med Res. 2002; 33:107-114; Yonemura Y, et al. Blood. 1997; 89:1915-1921], and GM-CSF can induce the proliferation of progenitors of the macrophagic, granulocytic, dendritic and erythroid lineages [Guzman P F, et al. Arch Med Res. 2002; 33:107-114; McNiece I, et al. Exp Hematol. 2001; 29:3-11]. TPO and HGF can affect proliferation and maturation of the megakaryocytic and hepatocytic lineages [McAdams T A, et al. Trends Biotechnol. 1996; 14:341-349; Danet G H, et al. Exp Hematol. 2001; 29:1465-1473; Gilmore G L, et al. Exp Hematol. 2000; 28:1297-1305].

The $2^{10-6}$ fractional factorial design (16 runs simultaneously) was adopted to identify which cytokines could help CD34+ cell expansion in the MNC culture system. This design could efficiently test ten compounds with 16 trials and provide sufficient degrees of freedom to obtain the coefficients. The basal medium was IMDM containing BIT as developed above; the initial cell density was $5 \times 10^5$ MNCs/ml, and the cells were analyzed after 7-day culture.

The design and results were shown as Table 3.

TABLE 3

Matrix of the $2^{10-6}$ fractional factorial design and experiment results*

| Trial | TPO | IL-3 | SCF | FL | IL6 | G-CSF | GM-CSF | SCGF | IL-11 | HGF | WBC† (10⁵/ml) | CD34+ cell† (10⁴/m) |
|---|---|---|---|---|---|---|---|---|---|---|---|---|
| 1 | +1 | +1 | +1 | −1 | +1 | −1 | −1 | −1 | −1 | +1 | 4.39 | 6.62 |
| 2 | −1 | −1 | −1 | +1 | −1 | +1 | +1 | +1 | −1 | +1 | 2.16 | 2.43 |
| 3 | −1 | +1 | −1 | −1 | +1 | +1 | −1 | +1 | −1 | −1 | 2.28 | 2.89 |
| 4 | +1 | +1 | +1 | +1 | +1 | +1 | +1 | +1 | +1 | +1 | 7.12 | 10.71 |
| 5 | −1 | +1 | −1 | +1 | −1 | −1 | +1 | −1 | +1 | −1 | 3.00 | 3.48 |
| 6 | +1 | −1 | +1 | −1 | −1 | +1 | −1 | +1 | +1 | −1 | 3.33 | 7.77 |
| 7 | −1 | −1 | +1 | +1 | +1 | −1 | +1 | +1 | +1 | +1 | 3.05 | 7.37 |
| 8 | +1 | −1 | −1 | −1 | +1 | −1 | +1 | +1 | −1 | −1 | 2.54 | 4.76 |
| 9 | −1 | +1 | +1 | −1 | −1 | −1 | +1 | +1 | +1 | −1 | 5.56 | 6.16 |
| 10 | −1 | +1 | +1 | −1 | −1 | +1 | −1 | −1 | −1 | −1 | 4.89 | 8.12 |
| 11 | +1 | −1 | +1 | +1 | −1 | −1 | +1 | −1 | −1 | −1 | 5.10 | 7.97 |
| 12 | +1 | +1 | −1 | −1 | +1 | +1 | +1 | −1 | +1 | +1 | 3.18 | 3.43 |
| 13 | −1 | −1 | +1 | −1 | +1 | +1 | −1 | −1 | +1 | +1 | 3.59 | 5.67 |
| 14 | −1 | −1 | −1 | −1 | −1 | −1 | −1 | +1 | +1 | +1 | 2.09 | 0.75 |
| 15 | +1 | −1 | −1 | +1 | +1 | +1 | −1 | −1 | +1 | +1 | 1.99 | 3.99 |
| 16 | +1 | +1 | −1 | −1 | −1 | −1 | +1 | +1 | −1 | +1 | 2.62 | 3.70 |

*−1: no addition; +1: the concentration of adding cytokine is 100 ng/ml; the initial seed density was $5 \times 10^5$ cells/ml.
†Cell density at day 7.

Two first-order models were obtained accordingly.

$$\text{WBCs/mL}(\times 10^5) = 3.56 + 0.23x_1 + 0.57x_2 + 1.07x_3 + 0.19x_4 - 0.06x_5 + 0.01x_6 + 0.48x_7 + 0.03x_8 + 0.11x_9 - 0.03x_{10} \quad (4)$$

$$\text{CD34}^+ \text{ cells/mL}(\times 10^4) = 5.36 + 0.75x_1 + 0.28x_2 + 2.19x_3 + 0.61x_4 + 0.32x_5 + 0.26x_6 + 0.21x_7 + 0.36x_8 + 0.09x_9 - 0.28x_{10} \quad (5)$$

Where $x_1$, $x_2$, $x_3$, $x_4$, $x_5$, $x_6$, $x_7$, $x_8$, $x_9$, and $x_{10}$ are ed variables of TPO, IL-3, SCF, FL, IL-6, G-CSF, GM-CSF, F, IL-11, and HGF, respectively.

Eq. (4) specified that IL-6 and HGF would inhibit WBC growth owing to their negative coefficient. Particularly, IL-6 exerted a negative effect on the WBC expansion, but a positive effect on the CD34$^+$ cell expansion. Furthermore, Eq. (5) indicated that the other eight kinds of cytokines all positively stimulated WBC and CD34$^+$ cell growth, and the importance for CD34$^+$ cell expansion followed the ranking: SCF>TPO>FL>SCGF>G-CSF>IL-3≈GM-CSF>IL-6>IL-11. The optimal concentrations of nine cytokines in the serum-free medium (IMDM+BIT) were determined along the steepest ascent path according to Eq. (5), and the results were listed in Table 4.

Example 4

Comparison of Different Basal Media and Commercial Media

Nine basal media supplemented with BIT and CC-9 were selected to compare their performance on CD34$^+$ cell expansion in the MNC culture system. Iscove's modified Dulbecco's medium (IMDM), RPMI 1640 medium, McCoy's 5A medium, minimum essential medium alpha medium (α-MEM), basal medium Eagle (BME), Dulbecco's modified Eagle medium (DMEM), Fischer's medium, Medium 199 and F-12K nutrient mixture medium (Kaighn's modification, F-12K) were purchased from GIBCO. X-vivo 20™ medium

TABLE 4

The concentrations of nine cytokines along the steepest ascent path for WBC and CD34$^+$ cell growth in the serum-free medium*

| Step | TPO (ng/ml) | IL-3 (ng/ml) | SCF (ng/ml) | FL (ng/ml) | IL-6 (ng/ml) | G-CSF (ng/ml) | GM-CSF (ng/ml) | SCGF (ng/ml) | IL-11 (ng/ml) | WBC† (10$^5$/ml) | CD34$^+$ cell† (10$^4$/ml) |
|---|---|---|---|---|---|---|---|---|---|---|---|
| 1 | 0 | 0 | 0 | 0 | 0 | 0 | 0 | 0 | 0 | 1.96 (0.13) | 0.72 (0.11) |
| 2 | 0.69 | 0.25 | 2 | 0.55 | 0.30 | 0.24 | 0.20 | 0.33 | 0.09 | 3.15 (0.31) | 6.82 (0.54) |
| 3 | 1.38 | 0.51 | 4 | 1.11 | 0.59 | 0.48 | 0.39 | 0.66 | 0.17 | 5.48 (0.24) | 10.57 (0.32) |
| 4 | 2.07 | 0.76 | 6 | 1.66 | 0.89 | 0.72 | 0.59 | 0.99 | 0.26 | 5.69 (0.19) | 10.30 (0.22) |
| 5 | 2.76 | 1.01 | 8 | 2.21 | 1.18 | 0.96 | 0.78 | 1.32 | 0.34 | 6.47 (0.19) | 11.52 (0.22) |
| 6 | 3.45 | 1.27 | 10 | 2.77 | 1.48 | 1.20 | 0.98 | 1.65 | 0.43 | 7.44 (0.21) | 12.45 (0.25) |
| 7 | 4.14 | 1.52 | 12 | 3.32 | 1.77 | 1.44 | 1.17 | 1.98 | 0.52 | 7.46 (0.23) | 12.40 (0.28) |
| 8 | 4.83 | 1.77 | 14 | 3.87 | 2.07 | 1.68 | 1.37 | 2.31 | 0.60 | 7.57 (0.15) | 12.49 (0.17) |
| 9 | 5.53 | 2.03 | 16 | 4.43 | 2.36 | 1.91 | 1.56 | 2.64 | 0.69 | 8.11 (0.13) | 13.40 (0.15) |
| 10 | 6.22 | 2.28 | 18 | 4.98 | 2.66 | 2.16 | 1.76 | 2.97 | 0.77 | 7.69 (0.26) | 10.70 (0.31) |
| 11 | 6.91 | 2.53 | 20 | 5.53 | 2.95 | 2.40 | 1.95 | 3.30 | 0.86 | 7.76 (0.25) | 11.54 (0.29) |
| 12 | 10.3 | 3.80 | 30 | 8.30 | 4.43 | 3.59 | 2.93 | 4.95 | 1.29 | 8.02 (0.24) | 11.88 (0.29) |
| 13 | 13.8 | 5.07 | 40 | 11.0 | 5.91 | 4.79 | 3.91 | 6.60 | 1.72 | 8.40 (0.22) | 10.76 (0.25) |
| 14 | 20.7 | 7.60 | 60 | 16.6 | 8.86 | 7.19 | 5.86 | 9.91 | 2.58 | 7.98 (0.33) | 9.84 (0.40) |
| 15 | 27.6 | 10.1 | 80 | 22.1 | 11.8 | 9.58 | 7.81 | 13.2 | 3.44 | 7.62 (0.35) | 9.01 (0.42) |
| 16 | 34.5 | 12.6 | 100 | 27.6 | 14.7 | 11.9 | 9.77 | 16.5 | 4.30 | 7.65 (0.29) | 9.36 (0.35) |

*Value in the parenthesis was the standard deviation; the initial seed density was 5 × 10$^5$ cells/ml.
†Cell density at day 7.

WBC and CD34$^+$ cell growth initially increased with cytokine concentration, reaching 8.11×10$^5$ and 1.34×10$^5$ cells/ml in step 9, respectively. After step 9, no more increases in CD34$^+$ cell density were observed. Consequently, the concentration of the cytokine formula in the IMDM containing BIT was optimized and named CC-9 (cocktail of nine cytokines: 5.53 ng/ml TPO, 2.03 ng/ml IL-3, 16 ng/ml SCF, 4.43 ng/ml FL, 2.36 ng/ml IL-6, 1.91 ng/ml G-CSF, 1.56 ng/ml GM-CSF, 2.64 ng/ml SCGF, and 0.69 ng/ml IL-11).

was purchased from BioWhittaker (Walkersville, Mass.). Stemline™ Hematopoietic stem cell expansion medium (Stemline) was purchased from Sigma. Stemspan™ H2000 contained Stemspan™ CC100 medium (cytokine cocktail of 100 ng/ml FL, 100 ng/ml SCF, 20 ng/ml IL-3 and 20 ng/ml IL-6) (H2000+CC100) was purchased from StemCell Technologies. (Vancouver, Canada).

The results were shown as Table 5.

TABLE 5

The effects of different basal and commercial media on WBC, CD34$^+$ cell, and CFC expansion*

| Basal Medium (with BIT and CC-9) | Number of experiments | Cell growth‡ WBC (10$^5$/ml) | Cell growth‡ CD34$^+$ cell (10$^4$/ml) | CD34$^+$ cell expansion Fold | CFC ratio E:GM:GEMM† | Total CFC Expansion fold |
|---|---|---|---|---|---|---|
| IMDM | 20 | 6.42 (0.35) | 12.35 (0.57) | 30.4 (1.52) | 39:58:3 | 10.7 (0.75) |
| RPMI 1640 | 8 | 3.36 (0.20) | 2.59 (0.22) | 6.4 (0.45) | 34:61:5 | 0.9 (0.13) |

TABLE 5-continued

The effects of different basal and commercial media on WBC,
CD34+ cell, and CFC expansion*

| Basal Medium | Number of experiments | Cell growth‡ | | CD34+ cell expansion Fold | CFC ratio E:GM:GEMM† | Total CFC Expansion fold |
|---|---|---|---|---|---|---|
| | | WBC ($10^5$/ml) | CD34+ cell ($10^4$/ml) | | | |
| McCoy's 5A | 8 | 3.85 (0.17) | 6.18 (0.30) | 15.3 (0.75) | 14:84:2 | 2.7 (0.23) |
| α-MEM | 8 | 2.41 (0.14) | 2.97 (0.11) | 7.3 (0.26) | 23:74:3 | 1.7 (0.13) |
| DMEM | 8 | 3.60 (0.18) | 2.12 (0.05) | 5.2 (0.15) | 23:68:8 | 0.8 (0.11) |
| BME | 8 | 2.13 (0.05) | 2.03 (0.13) | 5.1 (0.26) | 15:82:3 | 0.6 (0.05) |
| Fischer's medium | 8 | 1.67 (0.13) | 1.87 (0.10) | 4.6 (0.33) | 34:62:4 | 0.8 (0.07) |
| Medium 199 | 8 | 1.67 (0.07) | 2.96 (0.23) | 7.3 (0.40) | 29:66:5 | 1.1 (0.13) |
| F-12K (with CC-9) | 8 | 1.97 (0.13) | 2.87 (0.13) | 7.1 (0.27) | 44:50:6 | 1.4 (0.21) |
| X-vivo 20 | 8 | 8.12 (0.52) | 12.17 (0.72) | 29.9 (1.95) | 30:65:5 | 10.2 (0.82) |
| Stemline (complete medium) | 8 | 8.68 (0.35) | 12.35 (0.58) | 30.5 (2.02) | 35:62:3 | 7.5 (0.92) |
| H2000 + CC100 | 8 | 6.89 (0.34) | 10.69 (0.53) | 26.4 (1.22) | 41:55:5 | 8.9 (0.77) |

*Value in the parenthesis was the standard deviation. The initial seed density was $5 \times 10^5$ cells/ml, and initial CFC number was 3521 ± 458/ml, and E:GM:GEMM was 32:59:9.
†E:GM:GEMM meant the ratio of BFU-E, CFU-GM and CFU-GEMM numbers.
‡Cell density at day 7.

After 7-day culture, CD34+ cells grew in every medium that containing BIT and CC-9, but only media based on IMDM, McCoy's 5A, α-MEM, and F-12K promoted CFC expansion. IMDM performed the best on WBC, CD34+ cell, and CFC expansion.

The optimal serum-free and cytokines-containing medium (i.e. IMDM containing BIT and CC-9) was named SF-MNC. Moreover, the expansion abilities of CD34+ cell and CFC of SF-MNC were superior or comparable to those of commercially available serum-free media such as X-vivo 20, Stemline (both adding CC-9), and hematopoietic medium, Stemspan H2000+CC100 (Table 5).

Figure 1:
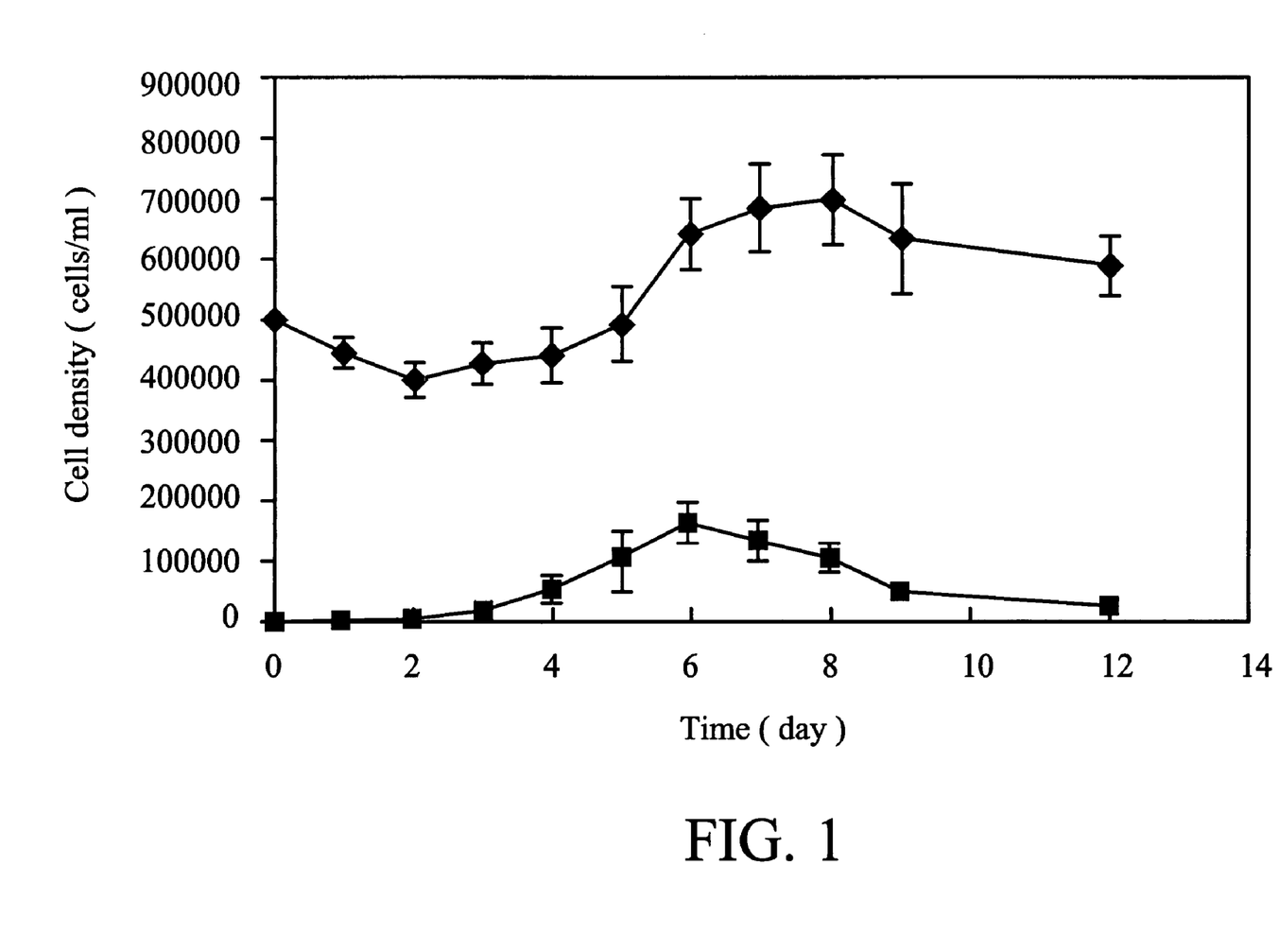
FIG. 1 illustrates the growth curve of WBCs and $CD34^+$ cells in SF-MNC medium. The initial MNC density was $5 \times 10^5$ cells/ml. Symbols: (♦), WBCs; (■), $CD34^+$ cells (n=20).

The growth profiles of WBC and CD34+ cells in the SF-MNC batch culture were shown in FIG. 1. The initial MNC density was $5 \times 10^5$ cells/ml. (♦) represents WBCs, and (■) represents CD34+ cells. During the first two days, the cell density of the suspending WBC decreased continuously, because the cells were at lag phase, and some cells in the MNC adhered to the well surface, such as macrophages, monocytes, and dendritic cells [Diggs L W, et al. Leukocyte, erythrocytes, thrombocytes. In: The morphology of human blood cells, 1st ed. Philadelphia: Saunders; 1956. p. 3-19; Bracho F, et al. Cytotherapy. 2003; 5:349-361; Mayordomo J I, et al. Stem Cells. 1997; 15:94-103]. After 2-day culture, the cell densities of the suspending WBC and CD34+ cells began to expand, and CD34+ cells reached its maximum at the sixth day, and then declined due to the batch culture without fresh medium adding.

Figure 2:
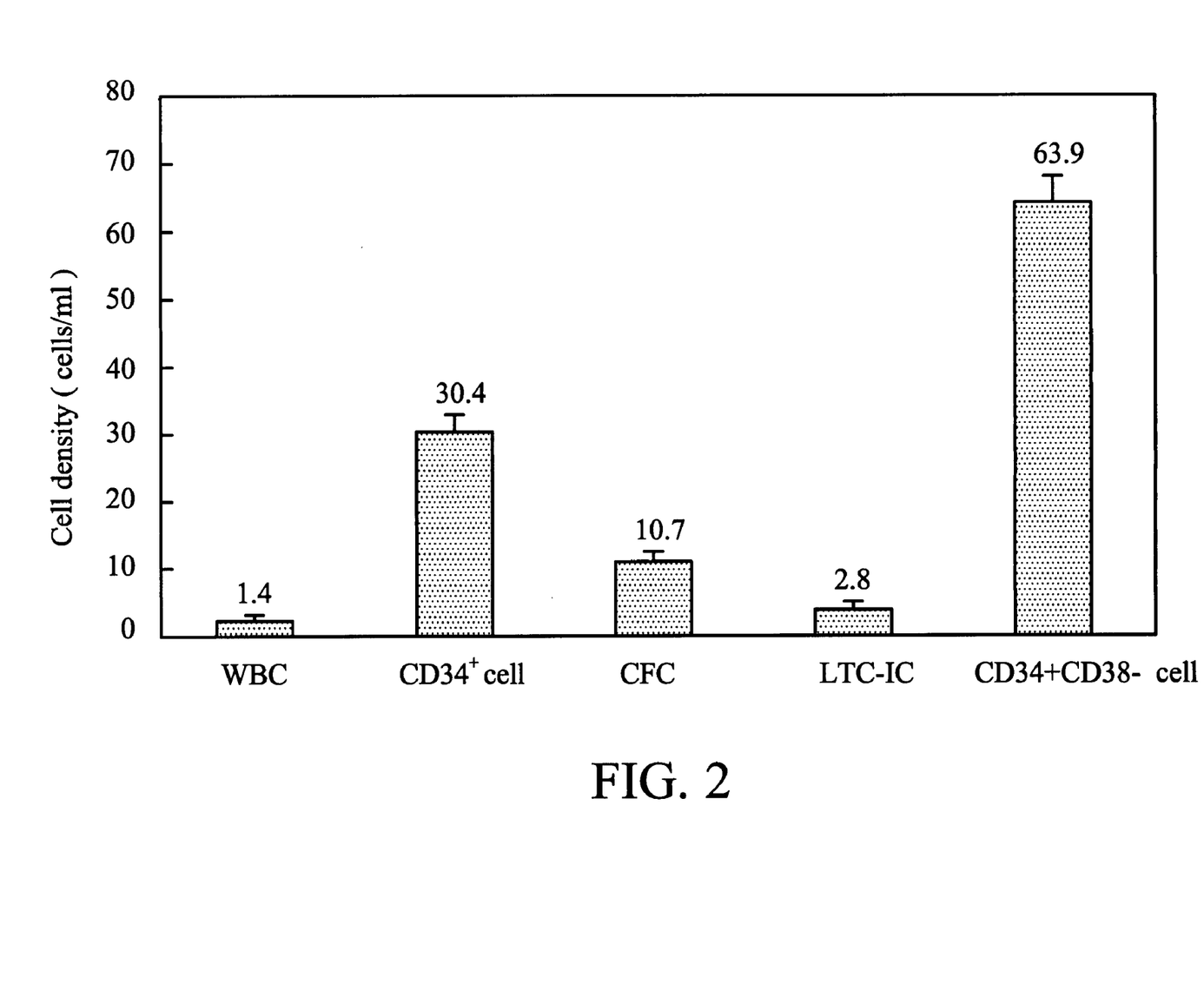
FIG. 2 illustrates expansion folds of WBCs, $CD34^+$ cells, CFCs, LTC-ICs, and $CD34^+CD38^-$ cells were cultured in SF-MNC medium for 6 days.

Expansion folds of WBCs, CD34+ cells, CFCs, LTC-ICs, and CD34+CD38− cells cultured in SF-MNC medium for 6 days were analyzed as shown in FIG. 2. At the sixth day, the absolute fold expansions for WBC, CD34+ cell, CFC, LTC-IC, and CD34+CD38− cell were 1.4-, 30.4-, 10.7-, 2.8-, and 63.9-fold, respectively. In this case, viability was measured using trypan blue exclusion and was found to be >95%.

Figure 3A:
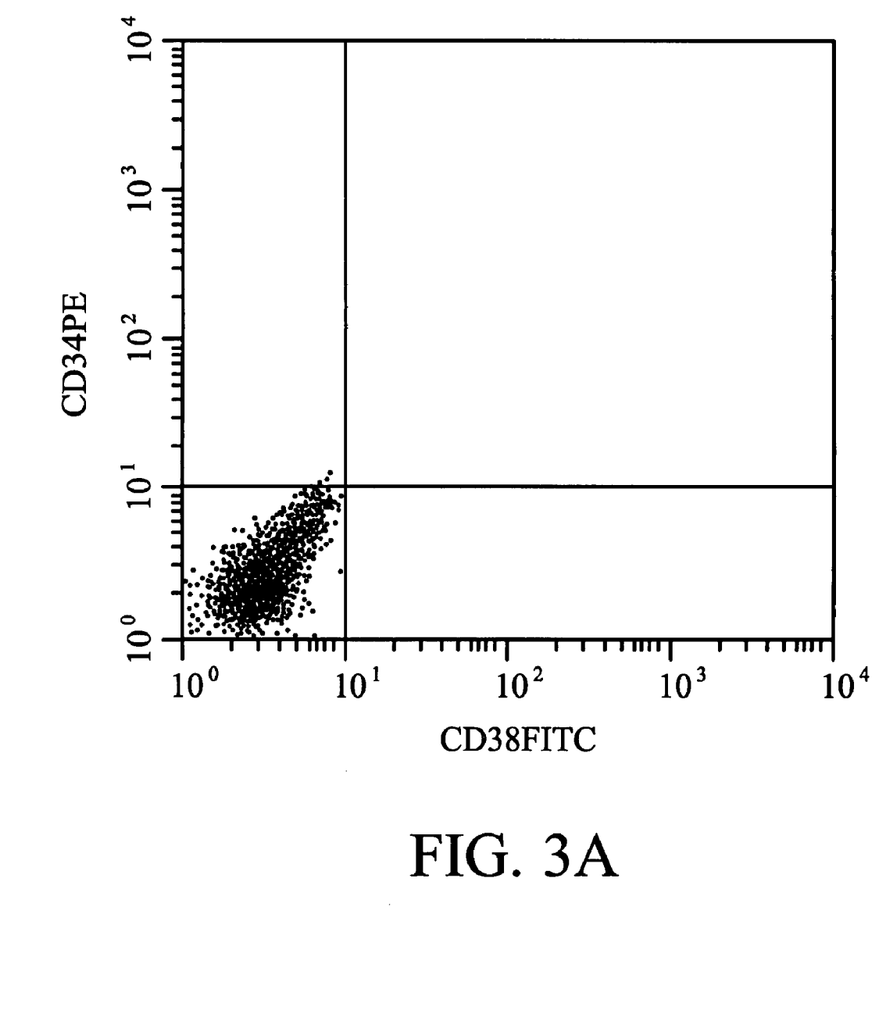
FIG. 3A shows isotype control for MNCs.
Figure 3B:
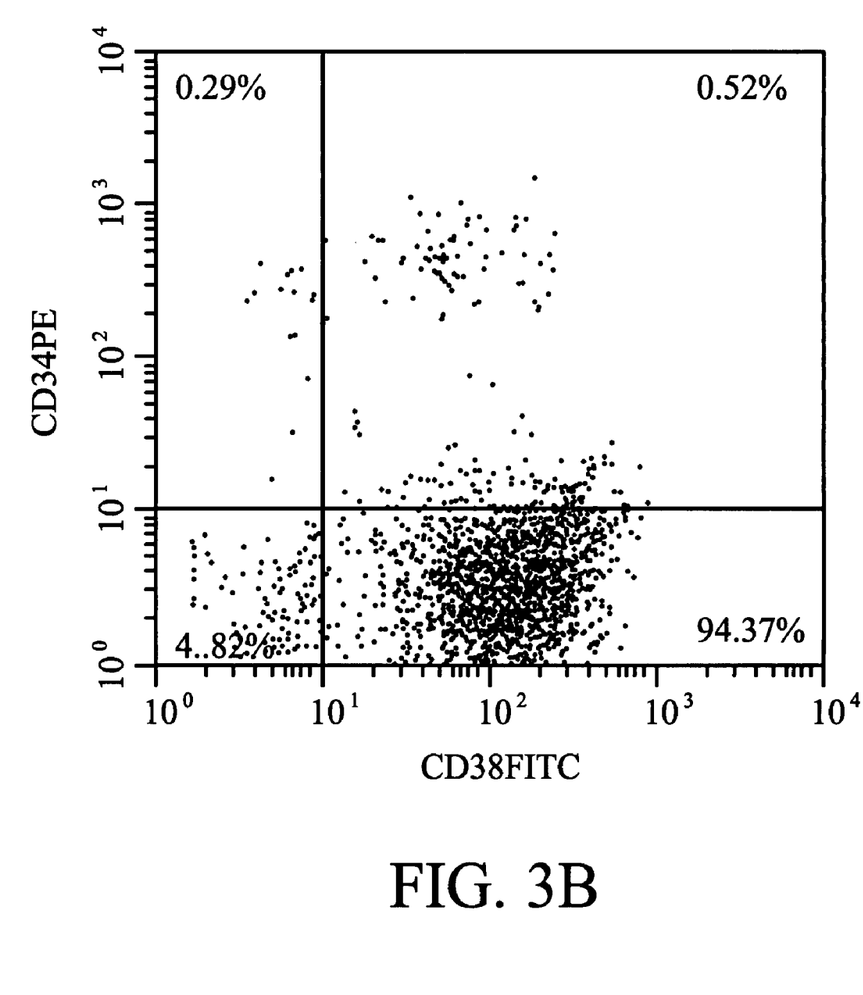
FIG. 3B shows that MNCs were analyzed after isolation from UCB by Ficoll-Paque density gradient centrifugation.
Figure 3C:
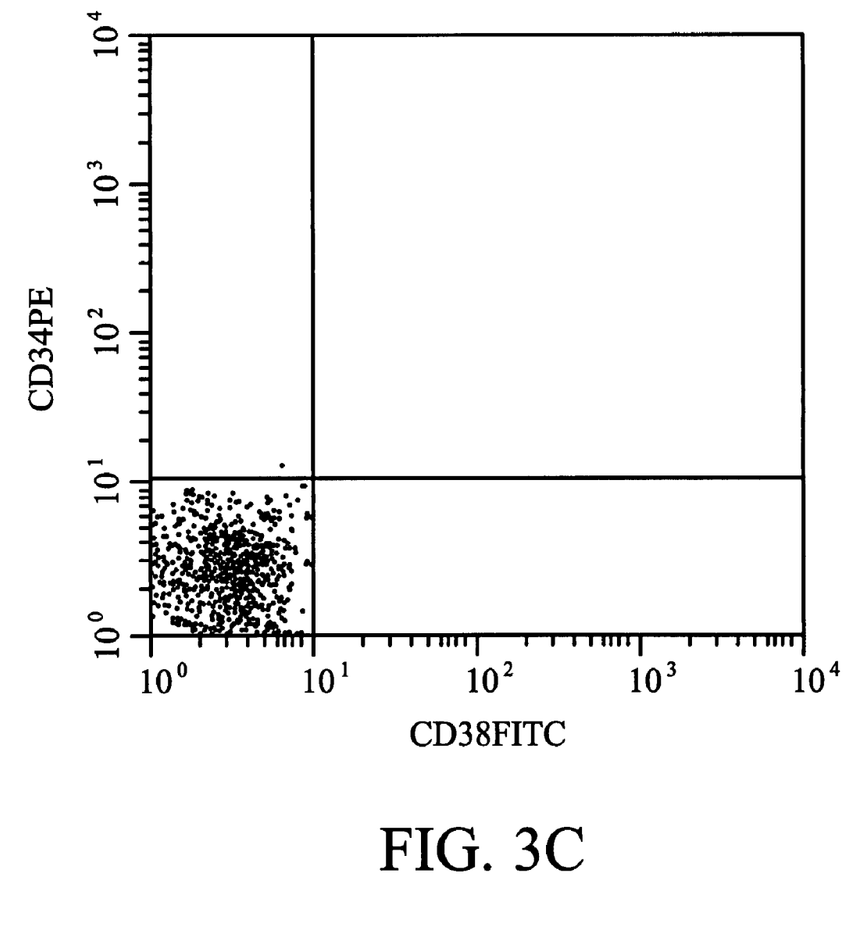
FIG. 3C shows isotype control for total expanding cells after 6-day culture in SF-MNC medium.
Figure 3D:
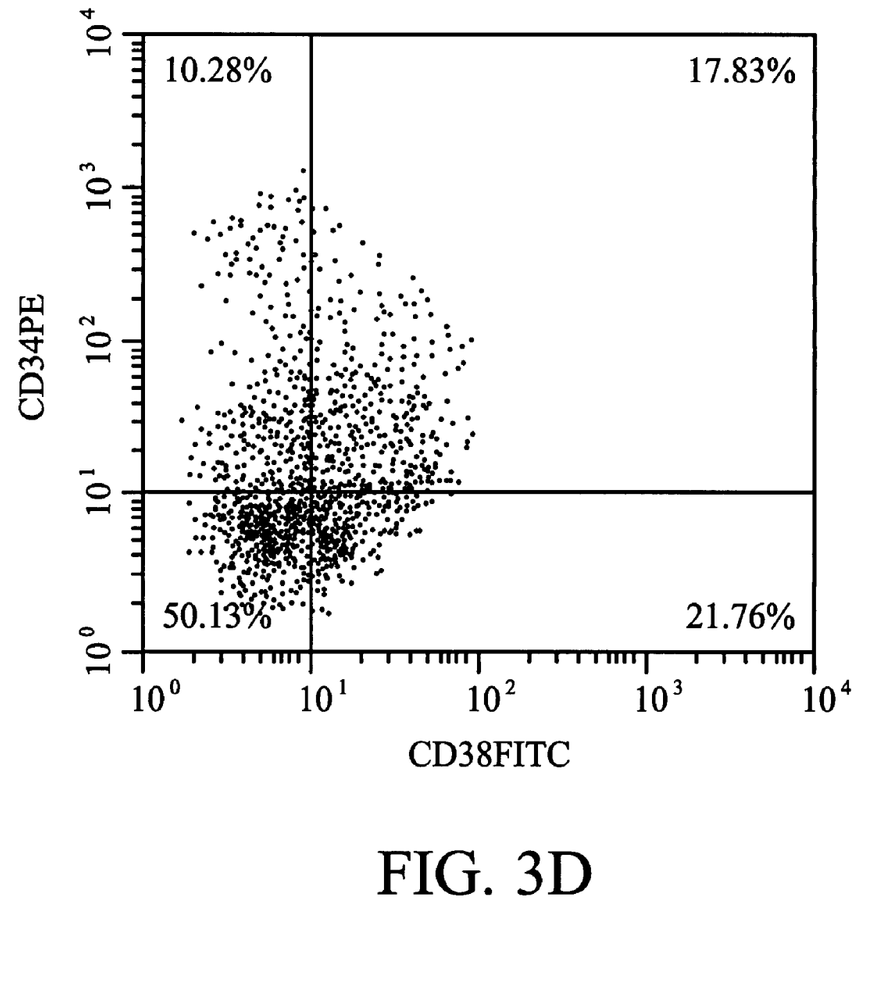
FIG. 3D shows that total expanding cells were analyzed after 6-day culture in SF-MNC medium.

The results of flow cytometry analysis of surface antigen expression (CD34 and CD38) were also shown in FIGS. 3A~3D. FIG. 3A represents isotype control for MNCs. FIG. 3B shows that MNCs were analyzed after isolation from UCB by Ficoll-Paque density gradient centrifugation. FIG. 3C represents isotype control for total expanding cells after 6-day culture in the SF-MNC medium. FIG. 3D shows that total expanding cells were analyzed after 6-day culture in the SF-MNC medium.

While the invention has been described by way of example and in terms of preferred embodiment, it is to be understood that the invention is not limited thereto.

What is claimed is:

1. A stroma-free, serum-free, and chemically defined medium for ex vivo mononuclear cell expansion, consisting of a basal medium; a serum substitute consisting of bovine serum albumin (BSA), insulin and transferrin (TF); and a cytokine formula consisting of thrombopoietin (TPO), stem cell factor (SCF), stem cell growth factor-α (SCGF), Flt-3 ligand (FL), interleukin (IL)-3, IL-6, IL-11, granulocyte colony-stimulating factor (G-CSF), granulocyte-macrophage and colony-stimulating factor (GM-CSF), wherein the medium is stroma-free, serum-free.

2. The medium as claimed in claim 1, wherein the basal medium is selected from a group consisting of Iscove's modified Dulbecco's medium (IMDM), McCoy's 5A medium, minimum essential medium alpha medium (α-MEM), and F-12K nutrient mixture medium (Kaighn's modification, F-12K).

3. The medium as claimed in claim 2, wherein the basal medium is Iscove's modified Dulbecco's medium (IDMD).

4. The medium as claimed in claim 1, wherein the serum substitute consists of 0.1-50 g/l BSA, 0.01-1000 µg/ml insulin, and 0.1-1000 µg/ml transferrin.

5. The medium as claimed in claim 4, wherein the serum substitute consists of 0.1-10 g/l BSA, 0.01-10 µg/ml insulin, and 0.1-400 µg/ml transferrin.

6. The medium as claimed in claim 5, wherein the serum substitute consists of 4 g/l BSA, 0.71 µg/ml insulin, and 27.81 µg/ml transferrin.

7. The medium as claimed in claim 1, wherein the cytokine formula consists of 0.1-500 ng/ml TPO, 0.1-500 ng/ml SCF, 0.1-500 ng/ml SCGF, 0.1-500 ng/ml FL, 0.1-500 ng/ml IL-3, 0.1-500 ng/ml IL-6, 0.1-500 ng/ml IL-11, 0.1-500 ng/ml G-CSF, and 0.1-500 ng/ml GM-CSF.

8. The medium as claimed in claim 7, wherein the cytokine formula consists of 0.1-100 ng/ml TPO, 0.1-100 ng/ml SCF, 0.1-100 ng/ml SCGF, 0.1-100 ng/ml FL, 0.1-100 ng/ml IL-3, 0.1-100 ng/ml IL-6, 0.1-100 ng/ml IL-11, 0.1-100 ng/ml G-CSF, and 0.1-100 ng/ml GM-CSF.

9. The medium as claimed in claim 8, wherein the cytokine formula consists of 5.53 ng/ml TPO, 16 ng/ml SCF, 2.64 ng/ml SCGF, 4.43 ng/ml FL, 2.03 ng/ml IL-3, 2.36 ng/ml IL-6, 0.69 ng/ml IL-11, 1.91 ng/ml G-CSF, and 1.56 ng/ml GM-CSF.

10. The medium as claimed in claim 1, wherein the expanded mononuclear cell is a hematopoietic stem cell.

11. The medium as claimed in claim 10, wherein the hematopoietic stem cell is CD34+ cell.

* * * * *